United States Patent [19]
Keith et al.

[11] Patent Number: 4,838,268
[45] Date of Patent: Jun. 13, 1989

[54] NON-OVER-THE WIRE BALLOON CATHETER

[75] Inventors: Peter T. Keith, Edina; Gerald G. Voegele, St. Bonifacius, both of Minn.

[73] Assignee: Scimed Life Systems, Inc., Minneapolis, Minn.

[21] Appl. No.: 164,511

[22] Filed: Mar. 7, 1988

[51] Int. Cl.[4] .......................................... A61M 29/02
[52] U.S. Cl. ...................................... 128/344; 604/96
[58] Field of Search ............ 128/344, 343, 325, 348.1; 604/96–103, 282

[56] References Cited

U.S. PATENT DOCUMENTS

| | | | |
|---|---|---|---|
| 1,481,078 | 1/1924 | Albertson . | |
| 1,636,038 | 3/1926 | Bolozky et al. . | |
| 1,785,345 | 12/1930 | Hasemann . | |
| 2,570,335 | 10/1951 | Fitch | 64/2 |
| 2,761,297 | 9/1956 | Buchsteiner | 64/2 |
| 2,821,092 | 1/1958 | Cordora et al. | 74/501 |
| 3,180,625 | 4/1965 | Wyzenbeek | 259/1 |
| 3,467,101 | 9/1969 | Fogarty et al. | 128/348.1 |
| 4,112,708 | 9/1978 | Fukuda | 64/2 R |
| 4,276,874 | 7/1981 | Wolvek et al. | 604/96 |
| 4,351,341 | 9/1982 | Goldberg et al. | 604/96 |
| 4,424,045 | 1/1984 | Kulischenko et al. | 464/52 |
| 4,561,439 | 12/1985 | Bishop et al. | 128/344 |
| 4,715,378 | 12/1987 | Pipe, Jr. et al. | 128/344 |
| 4,719,924 | 1/1988 | Crittenden | 604/282 X |

FOREIGN PATENT DOCUMENTS

WO86/06285 11/1986 PCT Int'l Appl. .

Primary Examiner—Stephen C. Pellegrino
Attorney, Agent, or Firm—Kinney & Lange

[57] ABSTRACT

A balloon catheter for use in angioplasty that includes a main shaft which is a flexible thin walled metal tube and a hollow, flexible torque transmitting shaft mounted at the distal end of the main shaft. A core member is connected to the torque transmitting shaft, and an inflatable balloon is mounted over the core and is attached to the distal end of the flexible torque transmitting shaft.

30 Claims, 4 Drawing Sheets

4,838,268

NON-OVER-THE WIRE BALLOON CATHETER

BACKGROUND OF THE INVENTION

1. Field of the Invention

The present invention relates to the field of angioplasty. In particular, the present invention relates to a dilatation balloon catheter.

2. Description of the Prior Art

Angioplasty has gained wide acceptance in recent years as an efficient and effective method for treating types of vascular diseases In particular, angioplasty is widely used for opening stenoses in the coronary arteries, although it is also used for treatment of stenoses in other parts of the vascular system.

The most widely used form of angioplasty makes use of a dilatation catheter which has an inflatable balloon at its distal end. Using fluoroscopy, the physician guides the catheter through the vascular system until the balloon is positioned across the stenosis. The balloon is then inflated by supplying fluid under pressure through an inflation lumen to the balloon. The inflation of the balloon causes stretching of the artery and pressing of the lesion into the artery wall to reestablish acceptable blood flow through the artery.

In order to treat very tight stenoses with small openings, there has been a continuing effort to reduce the profile of the catheter so that the catheter can reach and cross very tight stenoses. A successful dilatation catheter must also be sufficiently flexible to pass through tight curvatures through the very tortuous path of the vascular system. Still another requirement of the successful dilatation catheter is its "pushability". This involves the transmission of longitudinal force along the catheter from its proximal end to its distal end so that the physician can push the catheter through the vascular system and the stenosis.

Dilatation catheters can be divided into two groups: "over-the-wire" catheters and "non-over-the-wire" catheters. An over-the-wire catheter is one in which a guide wire lumen is provided so that the dilatation catheter can be fed over a guide wire until the balloon is positioned within the stenosis. A non-over-the-wire catheter acts as its own "guide wire". An advantage of a non-over-the-wire catheter is its potential for reduced profile because a guide wire lumen is not required.

The need for decreased dilatation catheter profile and increased flexibility has, in the past, required a compromise in the pushability and the torqueability of the catheter, particularly in the case of non-over-the-wire catheters. There is a continuing need for dilatation catheters of reduced catheter profile and improved flexibility without sacrificing torque response, catheter distal tip control, pushability of the catheter, and inflation/deflation times.

SUMMARY OF THE INVENTION

The catheter of the present invention includes a main shaft, a secondary shaft, a core, and an inflatable balloon. The main shaft is an elongate hollow thin wall tube, while the secondary shaft is a hollow, flexible, torque transmitting member which is connected to the distal end of the main shaft. The main shaft and the secondary shaft each have a flow lumen extending through them, which communicates with the interior of an inflatable balloon which is bonded to the distal end of the secondary shaft. The core is connected to one of the main and secondary shafts and extends through the inflatable balloon. The distal end of the inflatable balloon is connected to the core.

In one preferred embodiment of the present invention, the secondary shaft includes a plurality of layers of helically wound wire, which provides flexibility to the distal end of the catheter without sacrificing pushability or torqueability. A surface of the secondary shaft preferably is coated with a liquid impermeable layer to prevent leaking of the inflation fluid through the secondary shaft during inflation of the balloon.

In another preferred embodiment, the secondary shaft is integral with and of similar construction to the main shaft, but has smaller diameter to increase flexibility without significant sacrifice in pushability or torque response.

DETAILED DESCRIPTION OF THE PREFERRED EMBODIMENTS

Figure 1:
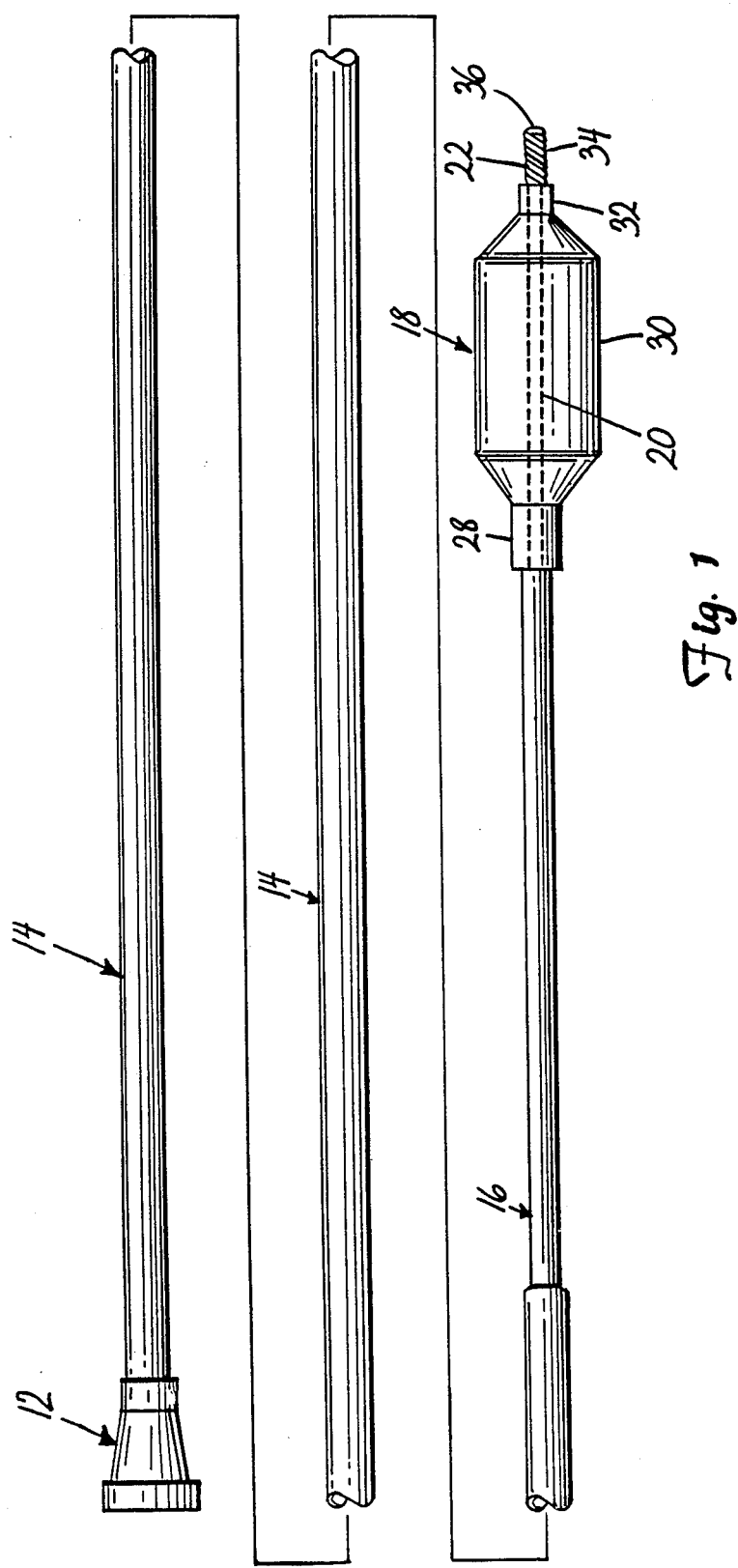
FIG. 1 shows one preferred embodiment of the dilitation balloon catheter of the present invention.

A catheter 10 shown in FIG. 1 is a dilitation balloon catheter which includes inflation port fitting 12, main shaft 14, secondary shaft 16, balloon member 18, core member 20, and spring tip 22.

Main shaft 14 is an elongated flexible thin walled tube, preferably of stainless steel with an outer coating of a low friction material such as polytetrafluoroethylene. Fitting 12 is mounted at the proximal end of main shaft 14 for connection to an inflation device (not shown) which provides fluid under pressure through the main flow lumen 24 (FIG. 2) of main shaft 14.

Mounted at the distal end of main shaft 14 is secondary shaft 16, which extends from the distal end of main shaft 14 to the proximal end of balloon member 18. Secondary shaft 16 is a hollow, flexible, torque transmitting shaft which has greater flexibility than main shaft 14. Flow lumen 26 (FIGS. 2 and 3) of secondary shaft 16 connects main flow lumen 24 of main shaft 14 with the interior of balloon member 18.

Balloon member 18, which is preferably a polymer material such as a polyolefin, includes proximal bond segment 28, distensible balloon segment 30, and small diameter distal segment 32. Proximal segment 28 is bonded to the distal end of secondary shaft 16.

Core member 20 extends through the interior of balloon member 18. The proximal end of core member 20 is bonded to the distal portion of secondary shaft 16, and the distal portion of core 20 extends out through the distal segment 32 of balloon member 18. Spring tip 22 includes coil spring 34 which is coaxially mounted over the distal portion of core member 20. Distal segment 32 of balloon member 18 surrounds and is bonded to the proximal end of coil spring 34, which in turn is brazebonded to core 20. Safety button 36 is a brazed end which connects together the distal ends of coil spring 34 and core member 20.

Figure 2:
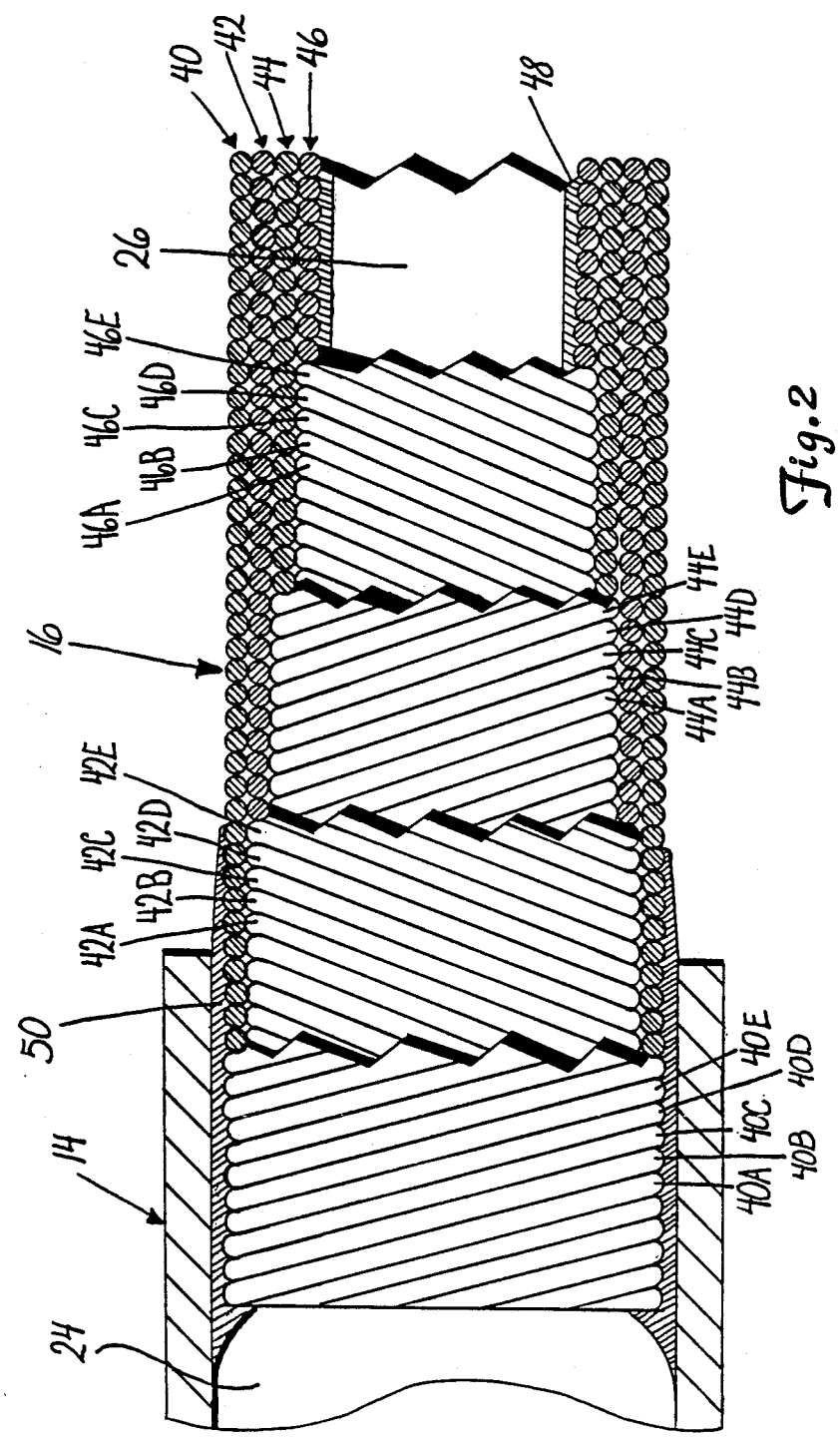
FIG. 2 is a sectional view, showing the distal end of the main shaft and the proximal end of the secondary shaft of the dilatation balloon catheter of FIG. 1.
Figure 3:
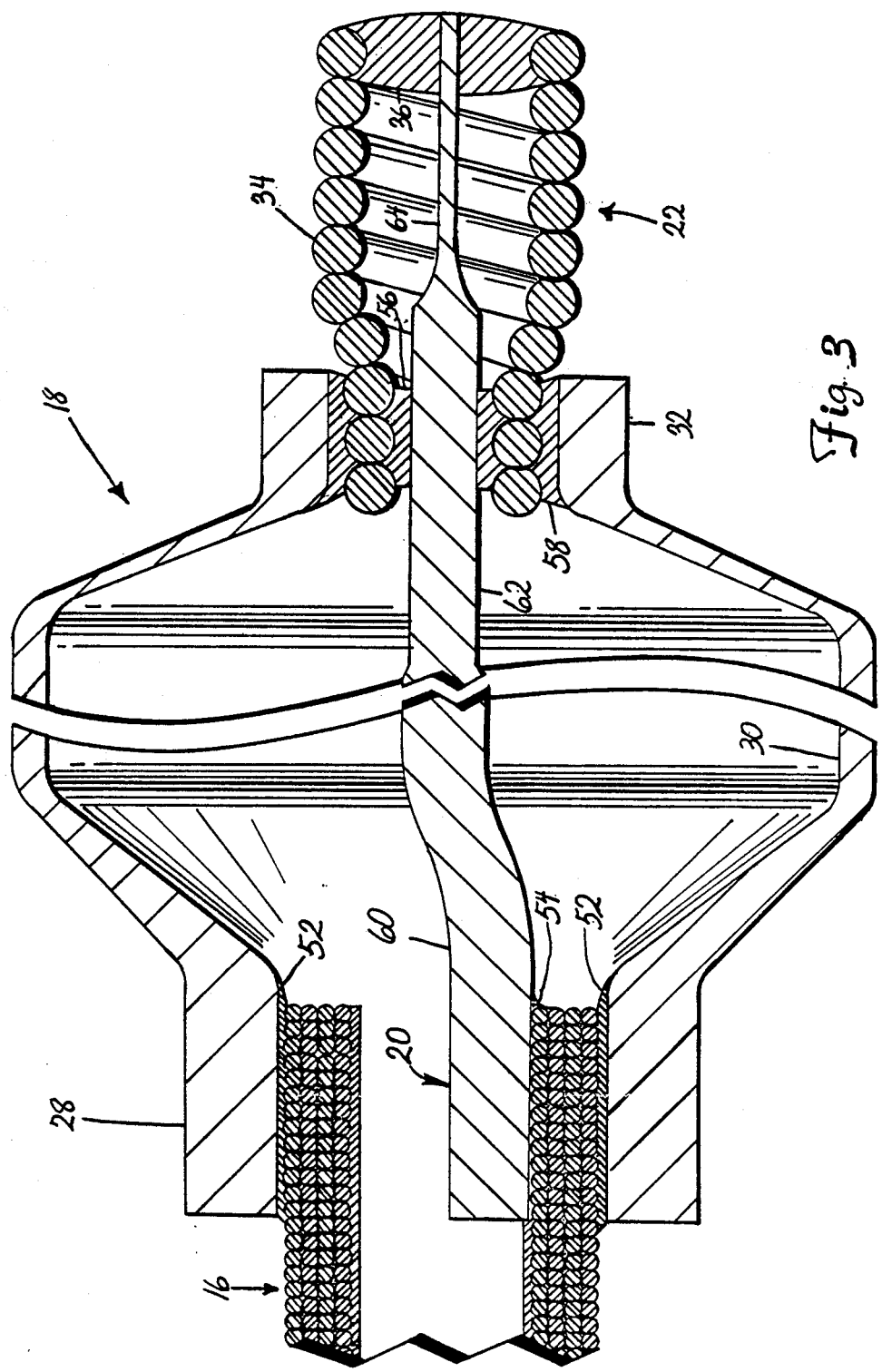
FIG. 3 is a sectional view showing the balloon and distal tip region of the dilatation balloon catheter of FIG. 1.

As shown in FIGS. 2 and 3, secondary shaft 16 is formed by four layers 40, 42, 44, and 46 of helically wound small diameter wires, with fluid impermeable layer 48 on its inner surface. Each helically wound layer 40, 42, 44, and 46 is wound with an opposite bias to its next adjacent layer, (as shown in FIG. 2) and are of progressively lower hardness, inside to out. In the preferred embodiments shown in FIG. 2, outer layer 40 is formed by five small diameter metal wires 40A–40E wrapped side by side. Similarly, layers 42, 44 and 46 are each five small diameter wires 42A–42E, 44A–44E, and 46A–46E which are wrapped side-by-side, respectively.

The proximal end of secondary shaft 16 extends into the distal end of main shaft 14 and is attached by brazed joint 50 to main shaft 14.

As shown in FIG. 3, the distal end of secondary shaft 16 extends into and is surrounded by the proximal bond portion 28 of balloon member 18. Epoxy bond 52 attaches the distal end of secondary shaft 16 to the proximal bond portion 28 of balloon member 18.

Core 20 is attached, by brazed bond 54 to the distal end of secondary shaft 16. Core 20 extends through the interior of balloon member 18 and is attached by brazed bond 56 to coil spring 34. Epoxy bond 58 attaches distal segment 32 of balloon member 18 to coil spring 34, and thus to core 20.

In the preferred embodiment shown in FIG. 3, core extension 20 is a stainless steel wire having a first segment 60 of about 0.005 inch diameter, a second segment 62 having an outside diameter of about 0.004 inch, having a third distal end segment 64 with a rectangular cross-section of about 0.001 by 0.003 inch.

One advantage of the catheter 10 of the present invention is that it provides sufficient flexibility of the distal end of catheter 10 without requiring a long proximal balloon waist segment which, while providing flexibility, also creates considerable friction and resistance to pushing and torqueing motion and must be supported by a solid internal corewire the entire length of the waist. In a preferred embodiment of the present invention, both the proximal segment 28 and the distal segment 32 of balloon member 18 are only about 0.08 inch in length—just long enough to provide bonds to shaft 16 and to spring tip 22, respectively.

Secondary shaft 16, which in a preferred embodiment has a length of about 12 inches, provides excellent "torqueability" while still being flexible enough to traverse extremely tight turns in the coronary anatomy without taking a permanent set, yet has a large enough flow lumen for fast inflation/deflation times.

With the present invention, a very low profile catheter is possible. The invention results in small outer diameter as torqueing and inflation passage are performed by the single mechanical element, the hollow secondary shaft 16. For example, in one preferred embodiment the main shaft 14 has an outside diameter of about 0.024 inches and an inside diameter of about 0.020 inches. The outside diameter of secondary shaft 16 is about 0.019 inches and the inside diameter is about 0.010 inches. The wall thickness of proximal bond section 28 of balloon segment 18 is about 0.0055 inches, resulting in an overall maximum outside diameter profile of only about 0.030 inches.

Use of multiple layers 40, 42, 44 and 46 of helically wound wires provides an ability to tailor the characteristics of secondary shaft 16 as may be needed for a particular catheter. For example, in one preferred embodiment of the present invention, wires of different temper or hardness are used for the different layers 40, 42, 44 and 46. For example, by using high temper wires for layer 46 and relatively soft wires for outer layer 40, it is possible to hold the wires together, while improving torque response. Tensioning controls during winding can also be used to achieve this internal binding effect.

Another unique advantage of the system of the present invention is the possibility of venting air out of the interior of balloon 18 through the interstitial openings in the distal end of secondary shaft 16. These interstitial openings can, by proper selection of wire size and wrapping, be made small enough so that inflation fluid cannot escape from the interior of balloon member 18, while being sufficiently large to allow air to be purged.

Other constructions for the main and secondary shafts are possible. For example, in another embodiment, main shaft 14 is made of a multiwire, multilayer, helically wound construction similar to secondary shaft 16. In this embodiment, larger diameter wires are used to form main shaft 14 in order to provide greater stiffness for main shaft 14.

Figure 4:
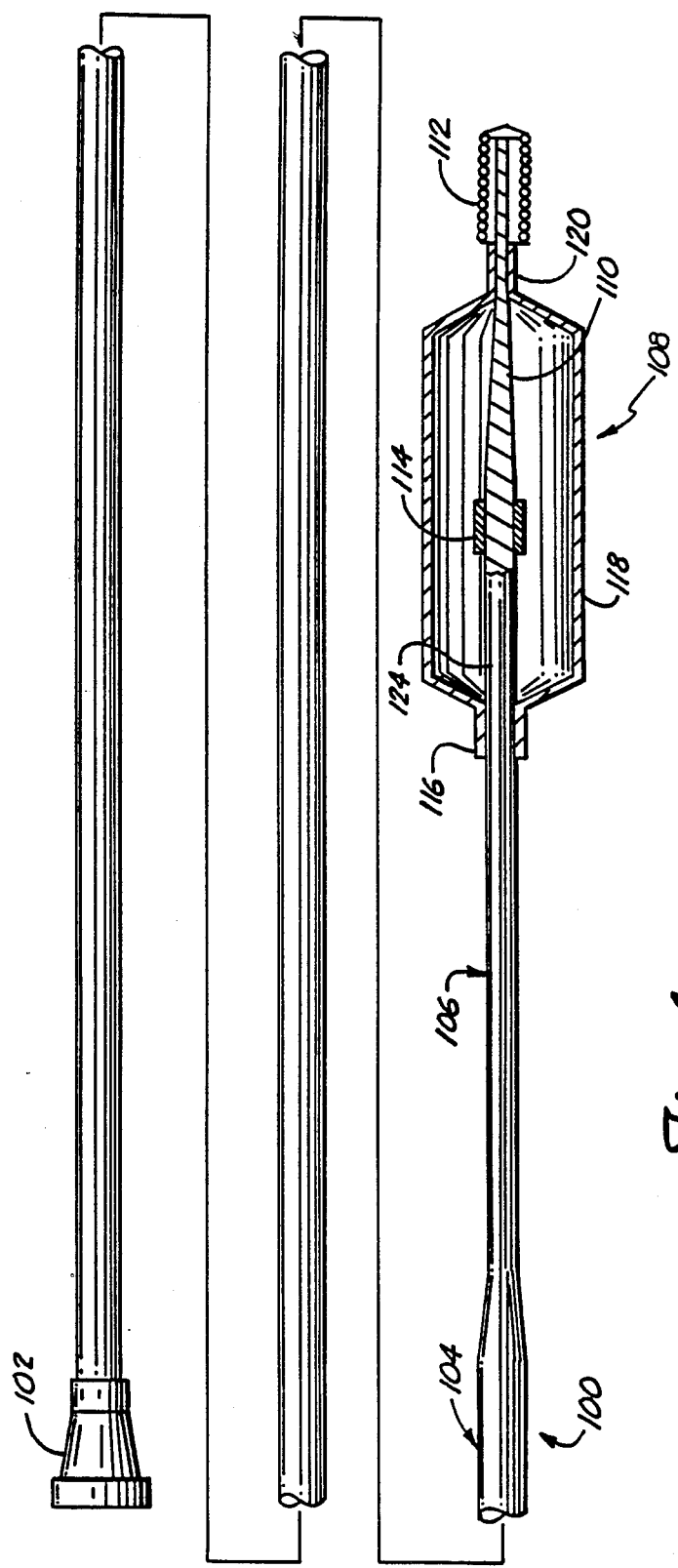
FIG. 4 shows another preferred embodiment of the dilitation balloon catheter of the present invention.

FIG. 4 shows still another embodiment of the present invention. Catheter 100 of FIG. 4 includes inflation port luer fitting 102, main shaft 104 secondary shaft 106, balloon member 108, core member 110, spring tip 112, and radiopaque balloon marker 114. Main shaft 104 and secondary shaft 106 are an integral tube, preferably of stainless steel with an outer coating of a low friction material. Secondary shaft 106 has a reduced wall thickness and/or outer diameter so that secondary shaft 106 (and core 110) define a "flexible zone" of about twelve inches in length at the distal end of catheter 100. Secondary shaft 106 has greater flexibility than main shaft 104, but retains torqueability and pushability characteristics.

Balloon member 108 has a short proximal bond segment 116 which is bonded to secondary shaft 106, a distensible balloon segment 118, and a short distal bond segment 120 which is bonded to solid distal core member 110. Main flow lumen 122 extends through main shaft 104 and secondary shaft 106, and opens to the interior of balloon segment 118 through port 124 in the distal portion of secondary shaft 106.

Although the present invention has been described with reference to preferred embodiments, workers skilled in the art will recognize that changes may be made in form and detail without parting from the spirit and scope of the invention.

What is claimed is:

1. A balloon catheter comprising:
   an elongate hollow, thin wall, tube having a lumen extending therethrough from a proximal end to a distal end;
   a hollow, flexible torque transmitting shaft having a first end connected to the distal end of the tube and having a flow lumen therethrough which is in communication with the lumen of the tube;
   an elongate core member extending distally from a second end of the shaft; and
   an inflatable balloon surrounding the core member and having a proximal end bonded to the second end of the shaft and a distal end bonded to the core member, an interior of the balloon being in communication with the flow lumen.

2. The balloon catheter of claim 1 wherein the hollow flexible shaft comprises a plurality of layers of helically wound wire.

3. The balloon catheter of claim 2 wherein the hollow flexible shaft has an inner surface and an outer surface and has a liquid impervious layer on one of the inner and outer surfaces.

4. The balloon catheter of claim 2 wherein each of the layers of helically wound wire is wound at a different bias from an immediately adjacent layer.

5. The balloon catheter of claim 4 wherein adjacent layers are wound with opposite bias.

6. The balloon catheter of claim 2 wherein each layer comprises a plurality of wires wound side-by-side.

7. The balloon catheter of claim 1 wherein the core member has a spring tip at a distal end.

8. The balloon catheter of claim 1 wherein the core member is connected to the shaft proximate the second end of the shaft.

9. The balloon catheter of claim 1 and further comprises means positioned near the balloon for venting air from the balloon.

10. The balloon catheter of claim 9 wherein the means for venting air comprises an air passage through the shaft.

11. The balloon catheter of claim 1 where in the tube and the shaft are an integral tubular member.

12. The balloon catheter of claim 11 wherein the shaft has a smaller wall thickness than the tube.

13. The balloon catheter of claim 11 wherein the shaft has a smaller outer diameter than the tube.

14. The balloon catheter of claim 11 wherein the shaft has a port therein to provide communication between the flow lumen and the interior of the balloon.

15. A balloon catheter comprising:
a main shaft having a first inflation lumen extending therethrough from a proximal end to a distal end;
a secondary shaft having a proximal end connected to the distal end of the main shaft and having a second inflation lumen extending therethrough from the proximal end to a distal end; the second inflation lumen being connected to the first inflation lumen, the secondary shaft having greater flexibility than and substantially similar torque transmitting characteristics to the main shaft;
an elongate core member extending distally from the distal end of the secondary shaft; and
an inflatable balloon surrounding the core member and having a proximal end connected to the distal end of the secondary shaft, a distal end connected to the core member, and an interior in communication with the second inflation lumen.

16. The balloon catheter of claim 15 wherein the main shaft is a thin wall metal tube.

17. The balloon catheter of claim 15 wherein the secondary shaft comprises a plurality of layers of helically wound wire.

18. The balloon catheter of claim 17 wherein the secondary shaft further comprises a liquid impervious layer on a surface.

19. The balloon catheter of claim 17 wherein each of the layers of helically wound wire is wound at a different bias from an immediately adjacent layer.

20. The balloon catheter of claim 19 wherein adjacent layers are wound with opposite bias.

21. The balloon catheter of claim 17 wherein each layer comprises a plurality of wires wound side-by-side.

22. The balloon catheter of claim 15 wherein the core member has a spring tip at the distal end.

23. The balloon catheter of claim 15 wherein the core member is connected to the secondary shaft proximate the distal end of the secondary shaft.

24. The balloon catheter of claim 15 and further comprising means positioned near the balloon for venting air from the balloon.

25. The balloon catheter of claim 24 wherein the means for venting air comprises an air passage through the shaft.

26. The balloon catheter of claim 15 wherein the main and secondary shafts are in integral tubular member.

27. The balloon catheter of claim 26 wherein the secondary shaft has a smaller wall thickness than the main shaft.

28. The balloon catheter of claim 26 wherein the secondary shaft has a smaller outer diameter than the main shaft.

29. The balloon catheter of claim 26 wherein the shaft has a port therein to provide communication between the second inflation lumen and the interior of the balloon.

30. The balloon catheter of claim 26 wherein the tubular member is a thin walled metal tube.

* * * * *

UNITED STATES PATENT AND TRADEMARK OFFICE
CERTIFICATE OF CORRECTION

PATENT NO. : 4,838,268

DATED : June 13, 1989

INVENTOR(S) : Peter T. Keith et al.

It is certified that error appears in the above-identified patent and that said Letters Patent is hereby corrected as shown below:

Column 5, lines 17-18, delete "comprises", insert --comprising--.

Signed and Sealed this

Fifteenth Day of May, 1990

Attest:

HARRY F. MANBECK, JR.

*Attesting Officer*      *Commissioner of Patents and Trademarks*